(12) United States Patent
Zhou et al.

(10) Patent No.: US 9,352,123 B2
(45) Date of Patent: May 31, 2016

(54) COLLARLESS GUIDE EXTENSION CATHETER

(71) Applicant: BOSTON SCIENTIFIC SCIMED, INC., Maple Grove, MN (US)

(72) Inventors: Pu Zhou, Maple Grove, MN (US); Ismal Guler, Maple Grove, MN (US)

(73) Assignee: BOSTON SCIENTIFIC SCIME, INC., Maple Grove, MN (US)

( * ) Notice: Subject to any disclaimer, the term of this patent is extended or adjusted under 35 U.S.C. 154(b) by 0 days.

(21) Appl. No.: 14/029,249

(22) Filed: Sep. 17, 2013

(65) Prior Publication Data

US 2014/0081243 A1 Mar. 20, 2014

Related U.S. Application Data

(60) Provisional application No. 61/702,080, filed on Sep. 17, 2012.

(51) Int. Cl.
*A61M 25/01* (2006.01)
*A61M 25/00* (2006.01)
*A61M 25/04* (2006.01)

(52) U.S. Cl.
CPC ........... *A61M 25/01* (2013.01); *A61M 25/0012* (2013.01); *A61M 25/0052* (2013.01); *A61M 25/0069* (2013.01); *A61M 25/04* (2013.01); *Y10T 29/49826* (2015.01)

(58) Field of Classification Search
CPC .......... A61M 25/007; A61M 25/0054; A61M 25/005; A61M 25/0147; A61M 25/0136; A61M 25/01; A61M 25/04; A61M 25/0052; A61M 25/0069; A61M 25/0012
USPC ........... 604/523, 524, 526, 528, 533; 600/585
See application file for complete search history.

(56) References Cited

U.S. PATENT DOCUMENTS

| | | |
|---|---|---|
| 4,564,014 A | 1/1986 | Fogarty et al. |
| 4,616,652 A | 10/1986 | Simpson |
| 4,762,129 A | 8/1988 | Bonzel |
| 5,120,323 A | 6/1992 | Shockey et al. |
| 5,232,445 A | 8/1993 | Bonzel |
| 5,267,982 A | 12/1993 | Sylvanowicz |
| 5,385,562 A | 1/1995 | Adams et al. |
| 5,441,489 A | 8/1995 | Utsumi et al. |
| 5,527,292 A | 6/1996 | Adams et al. |

(Continued)

FOREIGN PATENT DOCUMENTS

| | | |
|---|---|---|
| DE | 3819372 C1 | 1/1990 |
| EP | 0277366 A1 | 8/1988 |

(Continued)

*Primary Examiner* — Kevin C Sirmons
*Assistant Examiner* — Amber Stiles
(74) *Attorney, Agent, or Firm* — Seager, Tufte & Wickhem, LLP

(57) ABSTRACT

Embodiments of the disclosure describe an example guide extension catheter. The guide extension catheter may include a proximal shaft having a proximal end, a distal end, the distal end having an attachment region. The guide extension catheter may further include a distal sheath having a proximal end, a distal end and a lumen extending therebetween. The distal sheath may include an outer layer, inner layer and an intermediate reinforcing member disposed between the inner layer and the outer layer. Moreover, the distal sheath is attached to the attachment region adjacent to the reinforcing member.

14 Claims, 3 Drawing Sheets

(56) References Cited

U.S. PATENT DOCUMENTS

| | | |
|---|---|---|
| 6,066,126 A | 5/2000 | Li et al. |
| 6,575,958 B1 | 6/2003 | Happ et al. |
| 6,638,268 B2 | 10/2003 | Niazi |
| 6,695,793 B2 | 2/2004 | Brennan et al. |
| 6,866,655 B2 | 3/2005 | Hackett |
| 6,953,454 B2 | 10/2005 | Peterson et al. |
| 7,294,124 B2 | 11/2007 | Eidenschink |
| 7,316,678 B2 | 1/2008 | Nash et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 8,048,032 B2 | 11/2011 | Root et al. |
| 8,142,413 B2 | 3/2012 | Root et al. |
| 8,292,850 B2 | 10/2012 | Root et al. |
| 2003/0199849 A1 | 10/2003 | Hackett |
| 2004/0116832 A1 | 6/2004 | Friedrich et al. |
| 2004/0236215 A1* | 11/2004 | Mihara ............ A61M 25/0068 600/434 |
| 2005/0234427 A1* | 10/2005 | Eder ................ A61M 25/0009 604/526 |
| 2008/0125752 A1* | 5/2008 | Gunderson ....... A61M 25/0012 604/527 |
| 2009/0177120 A1 | 7/2009 | Tockman et al. |
| 2010/0217237 A1* | 8/2010 | Itou ........................ A61B 17/22 604/540 |
| 2010/0324482 A1* | 12/2010 | Farnholtz .................. 604/95.04 |
| 2011/0082443 A1* | 4/2011 | Griffin ............. A61M 25/0013 604/526 |

FOREIGN PATENT DOCUMENTS

| | | |
|---|---|---|
| EP | 1639951 A1 | 3/2006 |
| WO | 03049798 A2 | 6/2003 |

* cited by examiner

COLLARLESS GUIDE EXTENSION CATHETER

CROSS-REFERENCE TO RELATED APPLICATIONS

This application claims priority under 35 U.S.C.§119 to U.S. Provisional Application Ser. No. 61/702,080, filed Sep. 17, 2012, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a guide extension catheter that is free of collar.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The disclosure is directed to several designs, materials, systems and methods for manufacturing medical devices, guide extension catheter, for providing smooth transition.

Embodiments of the disclosure describe an example guide extension catheter. The guide extension catheter may include a proximal shaft having a proximal end, a distal end, the distal end having an attachment region. The guide extension catheter may further include a distal sheath having a proximal end, a distal end and a lumen extending therebetween. The distal sheath may include an outer layer, inner layer and an intermediate reinforcing member disposed between the inner layer and the outer layer. Moreover, the distal sheath is attached to the attachment region adjacent to the reinforcing member.

Other embodiments disclose an exemplary guide extension catheter. The guide extension catheter may include a proximal shaft having a proximal end, distal end, the distal end having an attachment region. Further, the extension catheter may include a distal sheath having proximal and distal ends; a portion of the distal sheath may include a reinforcing member attached to the attachment region.

Additional embodiments describe a method for manufacturing guide extension catheter. The method may include providing a proximal shaft having a proximal end, distal end and an attachment region. The method may further include providing a distal sheath having an outer polymer layer, inner polymer layer and an intermediate reinforcing member. Further, the method may include bringing the attachment region in contact with the reinforcing member. Moreover, the method may include welding the attachment region to the reinforcing member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
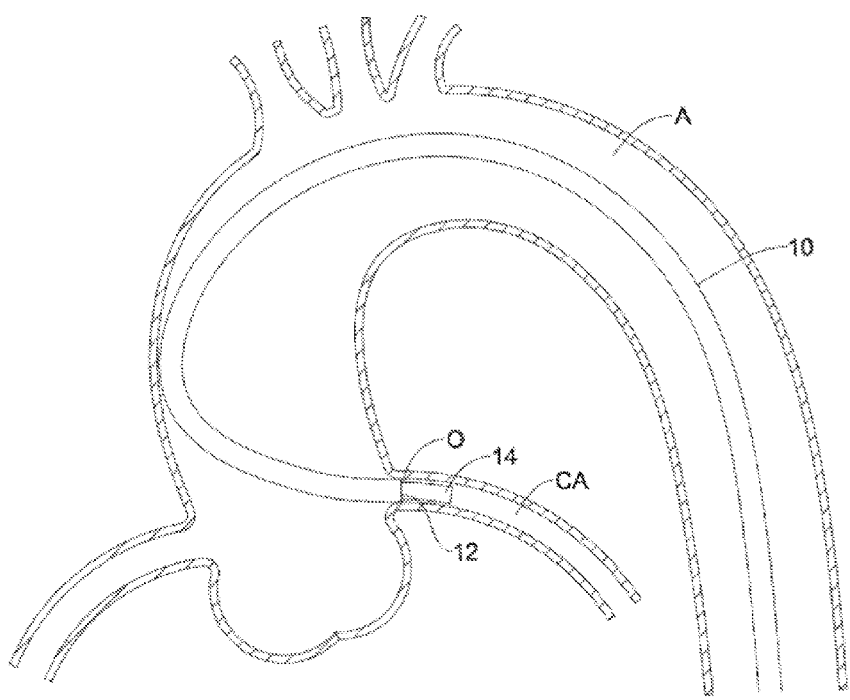
FIG. 1 is a plan view illustrating an example guide catheter with a guide Extension catheter, advanced through the aorta to the ostium of a coronary artery.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shah be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/ or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Embodiments of the disclosure may include a guide extension catheter having a proximal shaft, and a distal sheath. The proximal shaft having an attachment region, whereas the distal sheath having an outer layer, inner layer, and an intermediate reinforcing member disposed between the inner layer and the outer layer. A portion of the distal sheath may be attached to the attachment region adjacent to the reinforcing member.

For purposes of this disclosure, "proximal" refers to the end closer to the device operator during use, and "distal" refers to the end further from the device operator during use.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Disclosed herein are medical devices and methods for making and using medical devices that may improve access to the coronary arteries CA. Here, a guide extension catheter 14 extends through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, the extension catheter 14 may stabilize the positioning of guide catheter 10 and allow for improved access to the coronary artery CA for a number of cardiac interventions.

In some guide extension catheters a collar may be used to join the proximal shaft and the distal sheath. The collar may be a metal tube that transmits pushing forces from the proximal shaft to the distal sheath. In this structure, however, bending stiffness may increase at the collar joint. In addition, the collar structure may be a potential kink point. Thus, there is need to smooth out the flexibility transition, particularly at the junction point, between the proximal shaft and the distal sheath. In view of the mentioned limitations, the disclosure discloses various ways for joining the proximal shaft and the distal sheath without using a collar or other bridging structures. These structures are described in detail in connection with FIGS. 2A-2D.

FIG, 2A is a cross-sectional view of an example "collarless" guide extension catheter 100. As shown, the extension catheter 100 includes a proximal shaft 102 and a distal sheath 110. The proximal shaft 102 may serve as a handle or extension, and thus it may be an elongate member or a hypotube.-like structure having a proximal end 104, distal end 106, with an attachment region 108 at its distal end 106. The attachment region 108 may serve to connect the proximal shaft 102 to the distal sheath 110. In the illustrated embodiment, attachment region 108 takes a flattened form, but in other embodiments this area may take any desired cross-sectional shape, such as cylindrical, circular, rhombic, rectangular, oval, semicircular, or the like, suitable for attaching to the distal sheath 110. The proximal shaft 102 may further define a lumen between the proximal and distal ends, 104, 106 respectively. That lumen may extend along the entire length of the proximal shaft 102. In other embodiments, the lumen may extend along only a portion of the length of the proximal shaft 102. In still other embodiments, the proximal shaft 102 may be a solid wire or member (e.g., lacking a lumen).

The distal sheath 110 may be a tubular member that includes a proximal end 114, distal end 112, and a lumen extending therebetween. Given its function, distal sheath 110 may be sufficiently large to allow a therapeutic catheter (e.g. balloon catheter, stent delivery, etc.) to pass therethrough. For example, when guide extension catheter 14 is positioned within guide catheter 10, the therapeutic catheter may extend within guide catheter 10 alongside proximal shaft 102 and through lumen of the distal sheath 110. In some embodiments, the distal sheath 110 may have proximal and distal openings, at the proximal and distal ends 114, 112, respectively. The distal sheath 110 may be adapted to coaxially slide into the lumen of a desired guide catheter, and to project out from the distal end 112. The distal sheath 110 may assume a suitable cross-sectional shape such as circular, oval, polygonal or the like. In some embodiments, the cross-sectional shape of the distal sheath 110 may be similar to the cross-sectional shape of the desired guide catheter's lumen.

The material from which distal sheath 110 is formed may include an outer layer 120, an inner layer 119, and an intermediate reinforcing member 116 disposed between the inner layer 119 and the outer layer 120. A portion of the distal sheath 110 may be attached to the attachment region 108 adjacent to the reinforcing member 116. In the illustrated embodiment, the attachment region 108 may be directly connected to the reinforcing member 116. The proximal shaft 102 may be connected to the distal sheath 110 so as to have less bending stiffness at the attachment region 108. One technique for accomplishing that result may consist of stamping attachment region 108 into a flattened form and then welding it to the reinforcing member 116. This direct attachment of the proximal shaft 102 to the distal sheath 110 may provide a smooth transition of forces (push or pull) transferred from the proximal shaft 102 to the distal sheath 110. Smooth transition prevents kinking of the proximal shaft 102 upon bending. Accordingly, the length of the attachment region 108 may be chosen so as to have minimum kinking For example, greater is the length of the attachment region 108, more evenly proximal forces may be distributed within the distal sheath 110, but, if the length is relatively small, there may be certain undesired force vectors that may give rise to kinking. As discussed above, various welding techniques may include, but not limited to, laser welding, plasma welding, resistance welding, and e-beam welding or the like.

In at least some embodiments, the reinforcing member 116 may include one or more wires that are formed into a braid, coil, mesh, or the like. Other arrangements and/or configurations are contemplated. The reinforcing member 116 generally enhances stiffness of the distal sheath 110. The wires of the reinforcing member 116 may be made up of a single material or different materials, and thus the diameters of the wires may vary. The reinforcing member 116 may extend along the entire length of the distal sheath 110, but in some embodiments, the reinforcing member 116 may extend along a portion of the distal sheath 110. The reinforcing member 116 may be sandwiched between the inner layer 119 and outer layer 120, and may be tubular in shape or other shapes may also be contemplated. The reinforcing member 116 may be made of a material that is stiff enough to transmit longitudinally applied forces from the proximal end 114 of the distal sheath 110 at the distal end 112. In one example, the reinforcing member 116 may be made from stainless steel to provide longitudinal stiffness to the distal sheath 110. The shape and thickness of reinforcing member 116 may be changed in a variety of ways in order to achieve the desired flexibility at any location along the length of distal sheath 110.

The layers 119, 120 and reinforcing member 116 of the distal sheath 110 may be formed from a suitable biocompatible material, including polymers, metals (e.g., such as nitinol), blends, alloys, combinations thereof, or the like. Some example materials are disclosed herein. The reinforcing member 116 may be replaced by one or more stents, a stent-like cut tube. A stent-like cut tube may be include a variety of different cut patterns, arrangements, configurations, etc. as desired. Further, where the reinforcing member 116 is a braid material, that structure may include wires in various configurations, such as one-over-one, one-over-two, or two-over-two, and the like. In the illustrated embodiment, the braid wires may have a one-over-one structure. The braid wires may have any suitable shape, including round, ribbon, square, triangle, or the like. The strength of the element may be defined by the density of the braid. The braid wires may be arranged with various braid angle configurations. The pattern of the braid wires may be chosen to have a desired stiffness. The wires may be arranged in such manner to prevent deformation under radial forces prevalent during a surgical procedure.

To control the stiffness of the braid, sonic of the braid wires at the proximal end 114 may be joined by welding wires at crossover points (shown as dots 118). Other crossover points 118 are left with braid wires unjoined. The welded crossover points 118 may provide more stiffness transition, while the unwelded points provide flexibility. The welded crossover points 118 may provide less bending stiffness from the proximal shaft 102 to the distal sheath 110. To further explain, the welded crossover points 118 may enhance the bond integrity between the two joined sections and thus, may provide less abrupt transition and minimizes the tendency of kinking and may provide better torque transmission. Based on the stiffness requirement, more or fewer braid wires may be welded. The feature of welding braid wires may be used to create a flexibility gradient to transition along the length of the distal sheath 110. The density of welded points in a circumferential direction may determine the stiffness of the tube. In one embodiment, the welding process may employ friction welding, laser welding, or similar methods. The patterns of the welded braid wires may be designed so as to meet the push and flexibility transition requirements.

In alternative embodiments, proximal shaft 102 and the distal sheath 110 may be attached without welding the proximal shaft 102 to the distal sheath 110. In such embodiments, the proximal shaft 102 may be embedded within the layers of the distal sheath 110. More specifically, the proximal shaft 102 may be encapsulated between the reinforcing member 116 and the outer layer 120. For example, the proximal shaft 102 (e.g., attachment region 108) may be disposed adjacent to an outer surface of the reinforcing member 116 and the outer layer 120 may be disposed over the attachment region 108 to attach the proximal shaft 102 to the distal sheath 110 (e.g., via a reflow or other suitable process). In that manner, outer layer 120 may serve to physically connect the proximal shaft 102 to the distal sheath 110. Alternatively, the attachment region 108 may be disposed adjacent to an inner surface of the reinforcing member 116 and the inner layer 119 may be disposed over the attachment region 108 to attach the proximal shaft 102 to the distal sheath 110 (e.g., via a reflow or other suitable process).

Figure 2A:
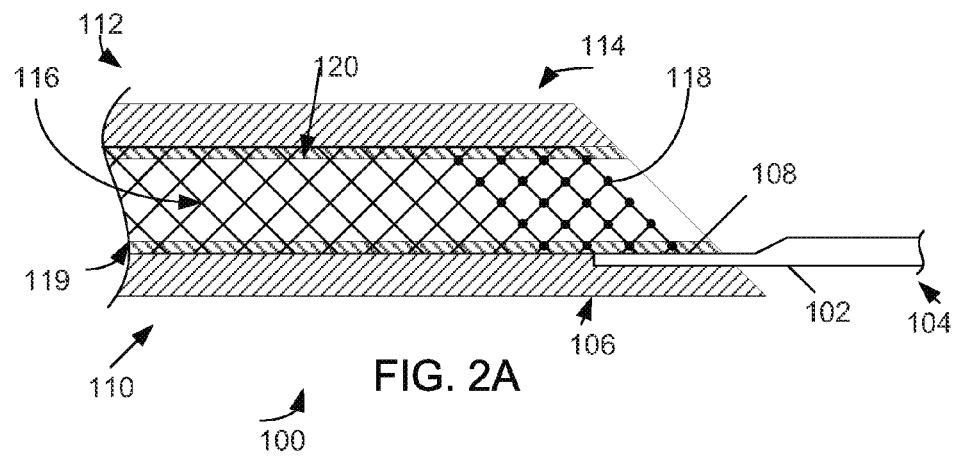
FIGS. 2A-2D illustrate various methods of joining structures of proximal shaft and distal sheath.
Figure 2B:
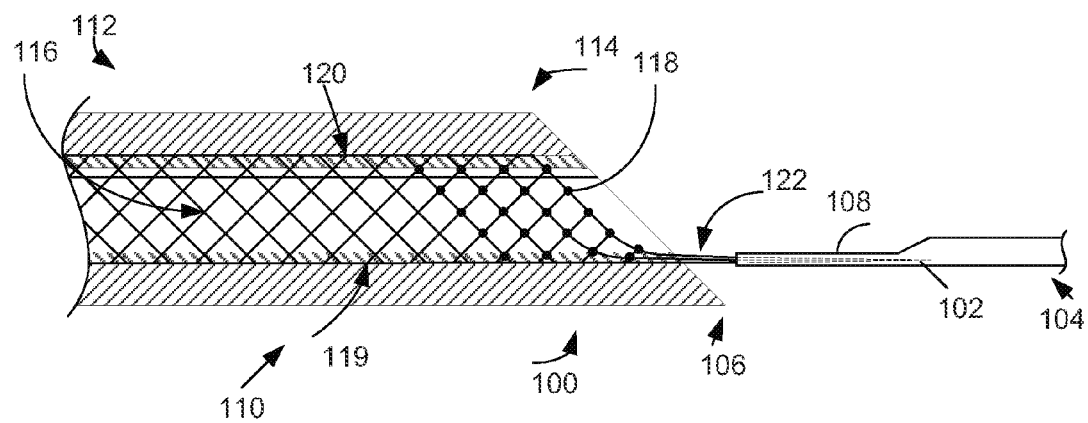

FIG. 2B shows an alternate method of joining the proximal shaft 102 to the distal sheath 110. More specifically, FIG. 2B illustrates an embodiment in which a bundle of wires 122, from reinforcing member 116, project from the proximal end 114 of distal sheath 110, into the distal end 106 of the proximal shaft 102. The proximal shaft 102 may be then stamped, crimping the material of proximal shaft 102 onto the bundle of wires 122. In some embodiments, proximal shaft 102 may formed from a hypotube, which would provide a lumen into which bundle 122 may be inserted before the stamping operation. In another embodiment, the bundle 122 may comprise from 4 to 32 individual wires. That number may vary to meet the needs of particular applications. When one or more wires from the top of the distal sheath 110 may be brought down to form a bundle 122, such wires may occlude the proximal opening (although not shown) of the distal sheath 110. In such cases, the portion of the bundle 122 passing over the proximal opening may be cut to "reopen" the proximal opening so that a therapeutic device may easily pass through it.

Figure 2C:
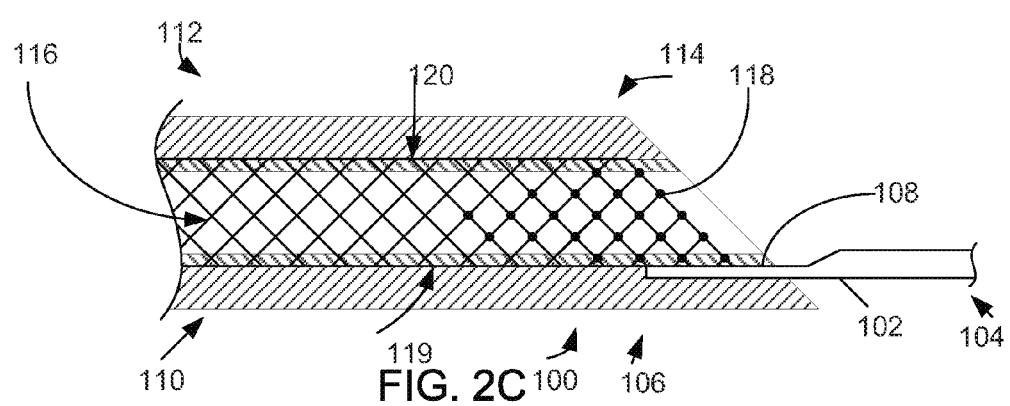

FIG. 2C illustrates an embodiment where the crossover points 118 may be welded in pre-defined fashion. In the illustrated embodiment, braid wires at the proximal end 114, may be welded, but as one moves distally, the number of welded braid wires may decrease along the length of the distal sheath 110 to achieve the flexibility requirements. The welded crossover points 118 are shown as dots in the figure. By changing the welding points' density along the longitudinal direction, braid tube stiffness changes. Other patterns of welding the braid wires may be contemplated to achieve the desired stiffness and flexibility. The fewer welded braid wires, the more flexible is the structure.

Figure 2D:
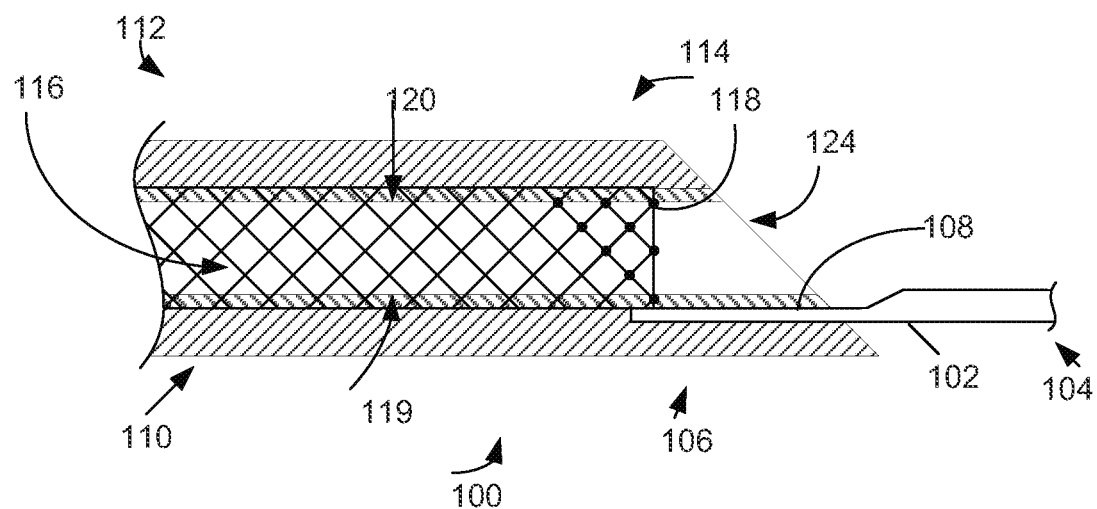

FIG. 2D sets out an embodiment in which reinforcing member 116 covers less than the entire length of distal sheath 110, leaving a bare portion 124. That portion may be sloped so that the transition and flexibility gradually shifts in the distal direction. The illustrated embodiment may include welding the attachment region 108 to the distal. sheath 110. Alternatively, the proximal shaft 102 may be attached to the distal sheath 110 by reflow soldering process as is known in the art, thus, need not to be described herein.

Additional embodiments disclose a method for manufacturing a collarless guide extension catheter is disclosed. The method may include providing a proximal shaft 102 having a proximal end 104, a distal end 106 and an attachment region 108. The method may further include providing a distal sheath 110 having an outer polymer layer 120, inner polymer layer and an intermediate reinforcing member 116. Further, the method may include bringing the attachment region 108 in contact with the reinforcing member 116. Moreover, the method may include welding the attachment region 108 to the reinforcing member 116. Instead of welding, the method may include reflowing the outer polymer layer 120 on the proximal shaft 102, in some embodiments. The method may also include inserting proximal ends of braid wires into lumen of the proximal shaft 102. Additionally, the method may include stamping the proximal ends of braid wires to the proximal shaft 102.

Manufacturing the distal sheath 110 may include using a mandrel having a shape corresponding to the desired shape for portions 119/120/116. For example, the mandrel may include a larger portion corresponding to proximal portion, a smaller portion corresponding to distal portion and a taper corresponding to tapered portion. The manufacturing process may include conventional reflow processes or other suitable processes.

Portions of all of the length of the distal sheath 110 may be loaded with or otherwise include a radiopaque material. Outer layer 120 and inner layer 119 may be formed from the same material. In some of these embodiments, outer layer 120 and inner layer 119 may include the same polymeric material and each be loaded with the same or different radiopaque materials. For example, inner layer 119 may include a polyether block amide loaded with approximately 75-95% (e.g., about 90%) by weight tungsten and outer layer may include a polyether block amide loaded with approximately 30-50% (e.g., 40%) by weight bismuth subcarbonate. These are just example. In other embodiments, outer layer and inner layer may be made from different materials.

Guide extension catheter 100 may also include a number of coatings that may, for example, reduce friction. For example, proximal member may have an inner and/or outer coating that includes a hydrophilic polymer that may reduce friction during 20 tracking. An example coating may include BAYER CL-100, BIOSLIDE, SLIP COAT, MDX, or the like. These are just examples. Other materials are contemplated including those disclosed herein. The materials that can be used for the various components of the guide extension catheters disclosed herein may vary. For simplicity purposes, the following discussion makes reference to proximal shaft and distal sheath. However, this is not intended to limit the devices and methods described herein, as the discussion may be applied to other similar tubular members and/or components of tubular members or devices disclosed herein.

A medical device assembly including the guide extension catheter, guide catheter, and guidewire or otherwise include metals, polymers, metal-polymer composites, and the like. Some examples of suitable metals and metal alloys include stainless steel, such as 304V, 304l L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Some examples of suitable polymers may include polytetrafluoroethylene (PTFE), ethylene tetrafluoroethylene (ETFE), fluorinated ethylene propylene (FEP), polyoxymethylene (POM, for example. DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYFREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenyleneterephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These are just examples, Although the embodiments described above use guide extension catheter, those of skill in the art will understand that the principles set out there can be applied to any device where it is deemed advantageous to track guide extension catheter easily over a guidewire. Conversely, constructional details, including manufacturing techniques and materials, are well within the understanding of those of skill in the art and have not been set out in any detail here. These and other modifications and variations may well within the scope of the present disclosure can be envisioned and implemented by those of skill in the art.

Other embodiments of the present disclosure be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. A guide extension catheter, comprising:
   a proximal shaft extending between a proximal end and a distal end, the distal end including an attachment region, the proximal shaft including a proximal shaft portion extending proximally from the attachment region, the proximal shaft portion having a shaft diameter, the attachment region having an attachment region diameter that is less than the shaft diameter; and
   a distal sheath extending distally from the proximal shaft, the distal sheath having a proximal end, a distal end and a lumen extending therebetween, the distal sheath having a sheath diameter that is greater than the shaft diameter, the distal sheath including an outer layer, an inner layer, and an intermediate reinforcing member disposed between the inner layer and the outer layer;
   wherein the distal sheath is secured to the proximal shaft via a physical attachment between the reinforcing member and the attachment region; and
   wherein the proximal shaft portion is axially spaced apart from the distal sheath.

2. The guide extension catheter of claim 1, wherein the reinforcing member includes a braid.

3. The guide extension catheter of claim 2, wherein the attachment region is stamped and welded to the braid.

4. The guide extension catheter of claim 2, wherein the braid includes multiple intersection points and wherein at least some of the intersection points are welded together.

5. The guide extension catheter of claim 4, wherein the number of intersection points that are welded together varies along the length of the reinforcing member.

6. The guide extension catheter of claim 1, wherein the proximal shaft is embedded between the outer layer and the reinforcing member.

7. The guide extension catheter of claim 1, wherein the reinforcing member includes a plurality of wires that each have a proximal end, and wherein the proximal ends of wires are bundled together and disposed within the attachment region of the proximal shaft.

8. The guide extension catheter of claim 7, wherein the proximal ends of the wires are attached to the proximal shaft by stamping.

9. The guide extension catheter of claim 1, wherein the reinforcing member extends to the proximal end of the distal sheath.

10. The guide extension catheter of claim 1, wherein the reinforcing member extends to a position distal of the proximal end of the distal sheath.

11. The guide extension catheter of claim 1, wherein the guide extension catheter is free of a collar disposed between and attaching the proximal shaft to the distal sheath.

12. A method for manufacturing a guide extension catheter, comprising:
   providing a proximal shaft having a proximal end, a distal end and an attachment region;
   providing a distal sheath having an outer polymer layer, inner polymer layer and an intermediate reinforcing member;
   bringing the attachment region in contact with the reinforcing member;
   welding the attachment region to the reinforcing member; and
   disposing an outer polymer layer on the proximal shaft.

13. The method of claim 12, wherein the reinforcing member includes a braid having a plurality of intersection points.

14. The method of claim 13, further comprising attaching at least some of the intersection points together.

* * * * *